(12) United States Patent
Malowaniec

(10) Patent No.: US 9,737,445 B2
(45) Date of Patent: Aug. 22, 2017

(54) METHOD FOR PRODUCING A DISPOSABLE INCONTINENCE DIAPER WITH CONTOURED DIAPER SIDE PARTS

(75) Inventor: Krzysztof D. Malowaniec, Heidenheim (DE)

(73) Assignee: Paul Hartmann AG, Heidenheim (DE)

( * ) Notice: Subject to any disclaimer, the term of this patent is extended or adjusted under 35 U.S.C. 154(b) by 807 days.

(21) Appl. No.: 13/880,539

(22) PCT Filed: Oct. 13, 2011

(86) PCT No.: PCT/EP2011/005145
§ 371 (c)(1),
(2), (4) Date: Aug. 29, 2013

(87) PCT Pub. No.: WO2012/052134
PCT Pub. Date: Apr. 26, 2012

(65) Prior Publication Data
US 2014/0303586 A1    Oct. 9, 2014

(30) Foreign Application Priority Data
Oct. 21, 2010   (DE) .................. 10 2010 049 171

(51) Int. Cl.
*A61F 13/15*   (2006.01)
*A61F 13/49*   (2006.01)

(52) U.S. Cl.
CPC .. *A61F 13/49058* (2013.01); *A61F 13/15756* (2013.01); *A61F 13/15764* (2013.01)

(58) Field of Classification Search
CPC .......... A61F 13/49058; A61F 13/15764; A61F 13/15756; Y10T 156/1056; Y10T 156/1057

See application file for complete search history.

(56) References Cited

U.S. PATENT DOCUMENTS

| 7,867,212 B2 | 1/2011 | Waksmundzki et al. |
| 7,887,526 B2 | 2/2011 | Van Gompel et al. |

(Continued)

FOREIGN PATENT DOCUMENTS

| DE | 10 2008 056 220 A1 | 5/2010 |
| DE | 10 2009 016 381 B4 | 2/2011 |

(Continued)

*Primary Examiner* — Mark A Osele
*Assistant Examiner* — Christopher C Caillouet
(74) *Attorney, Agent, or Firm* — Dilworth & Barrese, LLP

(57) ABSTRACT

The invention relates to a method for producing a multiplicity of disposable incontinence diapers (2) having a diaper main part (4) and, joined thereto, front and rear diaper side parts (22, 20), said method having the following method steps: feeding and conveying of an endless diaper main-part web (50); feeding of an endless diaper side-part web (21) to the separation and application station (24); singulating the disposable incontinence diapers (2) by separating the diaper main-part web (50) transversely relative to the first longitudinal direction (18), the curved edges of the longitudinal portions (46a, 46b), after separation from the diaper side-part web (21), being contoured in such a way that, after the first and second longitudinal portions (46a, 46b) have been secured to the first and second regions (56a, 56b) of the diaper main-part web, each rear diaper side part (20) has a lower edge (65) which has a convex portion, and each front diaper side part (22) has an upper edge (66) which has a concave portion.

7 Claims, 9 Drawing Sheets

(56) References Cited

U.S. PATENT DOCUMENTS

| | | | |
|---|---|---|---|
| 2002/0003024 A1* | 1/2002 | Vogt | A61F 13/15756 156/217 |
| 2005/0148965 A1 | 7/2005 | Richlen et al. | |
| 2008/0077101 A1 | 3/2008 | Waksmundzki et al. | |
| 2010/0108251 A1* | 5/2010 | Malowaniec | A61F 13/15739 156/256 |

FOREIGN PATENT DOCUMENTS

| | | |
|---|---|---|
| EP | 2238955 A1 | 10/2010 |
| JP | 2000184110 A | 6/2000 |
| WO | 2004/052260 A1 | 6/2004 |
| WO | 2005/016200 A1 | 2/2005 |
| WO | 2012/003965 A1 | 1/2012 |

\* cited by examiner

METHOD FOR PRODUCING A DISPOSABLE INCONTINENCE DIAPER WITH CONTOURED DIAPER SIDE PARTS

BACKGROUND OF THE INVENTION

The invention relates to a method for producing a multiplicity of open-type disposable incontinence diapers for adults, having a diaper main part and front and rear diaper side parts attached thereto. Disposable incontinence diapers of this type are known and have a main part, consisting of a front region, a rear region and a crotch region that is located in between in the longitudinal direction and comes to lie between the legs of a user, wherein the main part usually already comprises an absorbent core, and having four diaper side parts that are separate from one another, are attached to the rear region and the front region on both sides and which extend in the transverse direction beyond lateral longitudinal edges of the main part and connect the front region and the rear region together in the put-on state of the article.

The diaper side parts are preferably attached directly to the diaper main part, that is to say the chassis of the sanitary article, on both sides in a cut and place method. This manufacturing technology makes it possible to manufacture the diaper side parts from a different raw material than the central diaper main part of the sanitary article. For example, the diaper side parts may be configured in an air-permeable manner, whereas the central diaper main part may be formed in a substantially moisture-impermeable manner.

The most efficient and simplest, and also most cost-effective, shape of the diaper side parts from a manufacturing point of view is the rectangular shape. This allows the materials forming the diaper side parts to be transported during production in the form of an endless web of flat material from which the diaper side parts are then severed transversely to the machine direction. There are virtually no offcuts in this case.

However, it has been shown that, particularly when the diaper side parts are formed in the otherwise advantageous rectangular shape, when the sanitary article is being put on and while it is being worn, the problem sometimes occurs that the attached diaper side parts can tear in the region of the lateral longitudinal edges of the diaper main part. It has specifically been shown that, when users put on the sanitary article, they tend to exert a pull, obliquely to the transverse and longitudinal direction of the sanitary article, on the diaper side parts that extend extremely far in the transverse and longitudinal direction in the case of incontinence articles for adults, this being shown in FIG. 1 by way of an obliquely upwardly directed arrow. In such cases, it is possible for diaper side parts to tear along the lateral longitudinal edges of the diaper main part, with the tear propagating from the transverse edge, facing the crotch region, of the diaper side part. Therefore, DE102010026643 (as yet unpublished) proposes providing the rear diaper side parts with contouring, such that a lower edge of the rear diaper side part is formed in a curved manner, that the lower edge has a convex portion, that the ratio of the length A of the lower edge of a rear diaper side part to the width B of the lower edge of a rear diaper side part is 0.4-0.9 and the ratio of the longitudinal extent E of an extreme point P of the convex portion to the transverse extent F thereof is 0.15-0.80. In one embodiment, DE102010026643 also already shows front diaper side parts having a concave leg-opening contour.

The present invention is thus based on the object of creating a cost-effective method that can be realized advantageously in terms of process technology, for producing such or similar disposable incontinence diapers.

SUMMARY OF THE INVENTION

This object is achieved according to the invention by a method having the following method steps of:
  feeding and conveying an endless diaper main-part web in a first longitudinal direction to a separating and application station,
  feeding an endless diaper side-part web to the separating and application station, wherein, at the separating and application station, first and second dual-use longitudinal portions following one another and having at least regionally curved edges are severed from the diaper side-part web and are attached to first and second regions of the diaper main-part web, wherein the first and second regions each comprise a hip region of two diaper main parts following one another in the longitudinal direction and adjacent to one another,
  individually separating the disposable incontinence diapers by separating the diaper main-part web transversely to the first longitudinal direction, wherein the separating is carried out through the longitudinal portions such that a first sub-portion of at least one first respective longitudinal portion forms a rear diaper side part of a first disposable incontinence diaper and a second sub-portion of the respective first longitudinal portion forms a front or rear diaper side part of an immediately adjacent second disposable incontinence diaper, and such that a first sub-portion of a second respective longitudinal portion forms a front diaper side part of a disposable incontinence diaper and a second sub-portion of the respective second longitudinal portion forms a front or rear diaper side part of an immediately adjacent further disposable incontinence diaper,
  wherein the curved edges of the longitudinal portions are contoured after being severed from the diaper side-part web, such that each rear diaper side part has a lower edge which has a convex portion, and each front diaper side part has an upper edge which has a concave portion, and such that the length E of an outer edge of a respective front diaper side part is shorter than the length D of an inner edge of a respective front diaper side part,
  and wherein the longitudinal extent of the front diaper side parts is at least 60% of the longitudinal extent of the rear diaper side parts.

Thus, according to the method according to the invention, a diaper main-part web is conveyed endlessly, and diaper side parts are attached to this diaper main-part web in the claimed manner in the production machine. For their part, the diaper side parts originate from one or optionally also from a plurality of endlessly fed diaper side-part webs, from which dual-use longitudinal portions are severed and then applied to the endlessly conveyed diaper main-part web and fixed thereto. In order to individually separate the disposable incontinence diapers, a separating cut is carried out through a respective longitudinal portion, such that the one sub-portion of this longitudinal portion belongs to the one incontinence article and the other sub-portion belongs to the adjacent incontinence article. An essential advantage of this method is that the front and rear diaper side parts are already given their concave or convex contour, specified in more detail, by the contouring of the separating cut during the severing of the dual-use longitudinal portions, and thus, after the longitudinal portions have been attached to the main-part web, no further cutting of the portions, contouring the leg opening, is necessary.

Preferably, the curved edges of the longitudinal portions are contoured after being severed from the diaper side-part web, such that each rear diaper side part has a lower edge which has a single convex portion, and/or each front diaper side part has a lower edge which has a single concave portion. Furthermore, it is advantageous if in such a case the transverse extent of the convex portion extends over the entire width of the lower edge of the rear side part and/or the transverse extent of the concave portion extends over the entire width of the upper edge of the front side part.

The diaper main part or the diaper main-part web may in principle be produced continuously in the longitudinal direction particularly from nonwoven or film material or from a nonwoven/film composite. However, it has also been found to be advantageous for a respective diaper main part to have an absorbent core which stores liquids, preferably comprises superabsorbent materials and which may be attached in particular as a prefabricated unit to a backing web of the diaper main-part web. For example, this backing web could comprise a film layer or else a composite film having a thin nonwoven lining on the subsequent outer side, wherein absorbent cores are then applied to this backing web following one another in the longitudinal direction and adjacent to one another, and are preferably fixed to the backing web. This may, as mentioned, be a prefabricated absorbent core, frequently also known as an absorbent pad, or the absorbent core may be formed constructively by deposition of absorbent fiber material preferably with superabsorbent polymer materials.

The severing of the longitudinal portions from the diaper side-part web preferably takes place by cutting or punching along separating lines.

According to a variant of the method of the invention, a second sub-portion of the respective first longitudinal portion forms a front diaper side part and a second sub-portion of the respective second longitudinal portion forms a rear diaper side part. In such a case, the incontinence diapers are produced such that the rear part of a first incontinence diaper is immediately adjacent to the front part of a following incontinence diaper before they are individually separated. Preferably, these dual-use longitudinal portions are then formed and severed in that the endless diaper side-part web is first of all divided into two endless part-webs by a cut along a separating line, said cut extending continuously through the material of the diaper side-part web in a wave-like or sinusoidal manner in the longitudinal direction, and subsequently the dual-use longitudinal portions are finally severed, transversely to the longitudinal direction, from each part-web. In such a case, the first and second dual-use longitudinal portions are preferably formed to be congruent. It would also be conceivable and advantageous for the severing of the dual-use longitudinal portions to take place by separation along a separating line extending in a wave-like or sinusoidal or arcuate manner and extending on both sides beyond the longitudinal edges of the diaper side-part web.

According to a further preferred inventive concept of the method, a severed dual-use longitudinal portion consists, on the other hand, of two sub-portions which form either rear diaper side parts or front diaper side parts.

In such a case, a second sub-portion of the respective first longitudinal portion likewise forms a rear diaper side part and a second sub-portion of the respective second longitudinal portion forms a front diaper side part. In such a case, the dual-use longitudinal portions are severed preferably by separating along a separating line that extends in a wave-like or sinusoidal or arcuate manner on one or both sides beyond the longitudinal edges of the diaper side-part web.

Furthermore, it has been found to be advantageous for elastic elements that are made to extend in the longitudinal direction to be attached to the diaper main-part web, specifically on both sides. These elastic elements may also be provided such that they follow a certain contouring along the leg openings. However, they may also extend exactly in the longitudinal direction.

Furthermore, second elastic elements that are made to extend in the longitudinal direction and in particular are in the form of what are known as upright cuff elements, which are known per se, for example from EP0263720A1, may be attached to the diaper main-part web. These preferably upright second elastic elements flank to a certain extent a center of the diaper main part or of the absorbent core; they may be provided in the region of the edges of the absorbent pad, within the edges of the absorbent pad or outside the edges of the absorbent pad. They form a lateral run-out guard for the incontinence article.

According to an advantageous variant of the method according to the invention, the feeding of the longitudinal portions to the separating and application station takes place at a first speed v1 and the feeding of the endless diaper main-part web to the separating and application station takes place at a second speed v2, wherein the first speed v1 is lower than the second speed v2. In such a case, the longitudinal portions of the diaper side-part web are severed at the comparatively low speed v1 and then preferably accelerated to the speed v2, so that the longitudinal portions are deposited onto the diaper main-part web preferably at the same speed v2. This acceleration may take place for example by way of an application roller which can be subjected in particular to a negative pressure and which is arranged in particular immediately downstream in the transporting direction of the diaper side-part web of a separating or cutting station, where the longitudinal portions are severed.

According to a preferred embodiment of the invention, the second speed v2 may be at least 40%, particularly at least 70%, particularly at least 90%, particularly at most 200% greater than the first speed v1.

In an advantageous development of the invention, it is proposed that, after being severed from the diaper side-part web, the first longitudinal portions have edges that are curved in such a way and the longitudinal portions are fixed to the diaper main-part web in such a way that, after the disposable incontinence diapers have been individually separated, the lower edge of the rear diaper side parts has a length A and a width B and the convex portion has an extreme point P having a longitudinal extent E and a transverse extent F, wherein the ratio of the length A to the width B of the lower edge of a rear diaper side part is 0.40-0.90 and the ratio of the longitudinal extent E of the extreme point P to the transverse extent F thereof is 0.15-0.80.

In the context of the present invention, reference is made to DE102010026643 with regard to the definition of the extreme point P, the longitudinal extent E and transverse extent F thereof, the convex portion and the length A and width B of the lower edge of the rear diaper side parts.

Preferably, the ratio of the length A of the lower edge of a rear diaper side part to the width B of the lower edge of a rear diaper side part is 0.50-0.80, particularly 0.55-0.75.

In a development of the invention, it is proposed that the ratio of the transverse extent F of the extreme point P to the width B of a respective lower edge of the rear diaper side part is 0.20-0.60, particularly 0.30-0.50.

More particularly, the ratio of the longitudinal extent E of the extreme point P to the length A of a lower edge of a respective rear diaper side part is 0.10-0.40, particularly 0.10-0.30.

Advantageously, the ratio of the longitudinal extent E of an extreme point P of the convex portion of a rear diaper side part to the transverse extent F thereof is 0.20-0.60, particularly 0.20-0.50.

The basis weight of the material forming the diaper side-part web and thus the diaper side parts should advantageously be 13-40 g/m$^2$, particularly 15-30 g/m$^2$ and very particularly 16-28 g/m$^2$.

It has further been found to be advantageous for the front and/or rear diaper side parts, and thus the diaper side-part web, to consist of a nonwoven material or to comprise a nonwoven material. In particular all nonwoven materials which contain at least one formulation component based on a thermoplastics polymer are suitable. The nonwovens may contain fibers of PE, PP, PET, rayon, cellulose, PA and mixtures of these fibers. Bicomponent or multicomponent fibers are also conceivable and advantageous. In particular, carded nonwovens, water-jet needled nonwovens, spunbonded (S) nonwovens, meltblown (M) nonwovens, SMS nonwovens, SMMS nonwovens or else laminates of one of more of these kinds of nonwoven, wherein S stands for spunbonded nonwoven layers and M for meltblown nonwoven layers, are advantageous. It is furthermore conceivable and advantageous to form the front and/or rear diaper side parts from a nonwoven-film laminate. In such a case, the film component would come to lie on the outside and the nonwoven component on the inside, in order to ensure that a soft surface faces the body. As a development of this concept of the invention, it is advantageous to form the front and/or rear diaper side parts from a nonwoven-film-nonwoven laminate, in which a film component is arranged in the manner of a sandwich between two nonwoven components.

In a development of the invention, it is provided that the diaper side-part web is provided with closure means, in particular with mechanical closure aids, specifically in the region of the subsequent rear diaper side parts, before the dual-use longitudinal portions are severed. In order to secure the disposable incontinence diaper as intended on the body of a person, the closure means can be secured in a detachable manner at least in regions both to the outer side of the diaper main part and also the outer side of the front diaper side parts, with the retaining forces between the closure means and the outer side of the front diaper side parts preferably being greater than the retaining forces between the closure means and the outer side of the diaper main part.

The outer side of the diaper main part of the disposable incontinence diaper is preferably formed by a nonwoven, at least in regions, but particularly over the entire surface area. This gives the disposable incontinence diaper a textile-like impression. In such a case, it is advantageous to form the back sheet of the diaper main part from a nonwoven-film laminate, with the nonwoven layer coming to lie on the outside and the film layer on the inside directed toward the absorbent pad, so that the nonwoven layer forms the outer side of the diaper main part. This both ensures the liquid-impermeability of the diaper main part and ensures the skin-friendly nature of the diaper. The film layer of this nonwoven-film laminate is then formed preferably from a one- or multi-layer liquid-impermeable, but preferably nevertheless breathable, film, with the breathability of the front and/or the rear diaper side parts preferably being greater than the breathability of the nonwoven-film laminate forming the back sheet of the disposable incontinence diaper.

In a development of the invention, it has been found to be advantageous for the dual-use longitudinal portions to be dimensioned in such a way when being severed from the diaper side-part web, and to be attached to the main-part web in such a way, that the length of the subsequent front and/or rear diaper side parts, that is to say the maximum extent thereof in the diaper longitudinal direction, is at least 15 cm, particularly at least 20 cm, more particularly at least 25 cm, more particularly at least 27 cm and more particularly at most 45 cm. Preferably, the rear and/or the front diaper side parts have their maximum extent in the diaper longitudinal direction at their respective inner edge. In a particularly advantageous manner, the length of each front diaper side part, decreases outwardly (that is to say in the transverse direction) starting from the side edge of the main part. As seen in the longitudinal direction, the diaper side parts thus narrow preferably toward the outside, such that an outer edge of the front diaper side parts has a smaller length than an inner edge of the front diaper side parts.

Advantageously, the overall length of the disposable incontinence diaper is 60-120 cm, particularly 65-115 cm, and more particularly 70-110 cm. In a development of the invention, it has been found to be advantageous for the dual-use longitudinal portions to be dimensioned in such a way when being severed from the diaper side-part web, that the width of the front and/or rear diaper side parts, that is to say the maximum extent thereof beyond the side edge of the diaper main part is 10-40 cm, particularly 12-35 cm, more particularly 14-30 cm, and more particularly at most 25 cm. Preferably, the front diaper side parts have the same width as the rear diaper side parts.

It has been found to be advantageous for the length of the rear diaper side parts to be at least 10%, particularly at least 15%, more particularly at least 20% and more particularly at least 22%, more particularly at most 40% of the overall length of the disposable incontinence diaper.

Furthermore, a preferred embodiment provides that the front diaper side parts have a shorter longitudinal extent, particularly by at least 5%, more particularly by at least 10%, more particularly by at least 15% and more particularly by at most 30%, than the rear diaper side parts.

In the preceding and following text, the expressions "length" and "longitudinal extent" are used synonymously, and thus have the same meaning.

DETAILED DESCRIPTION OF THE PREFERRED EMBODIMENTS

Figure 1:
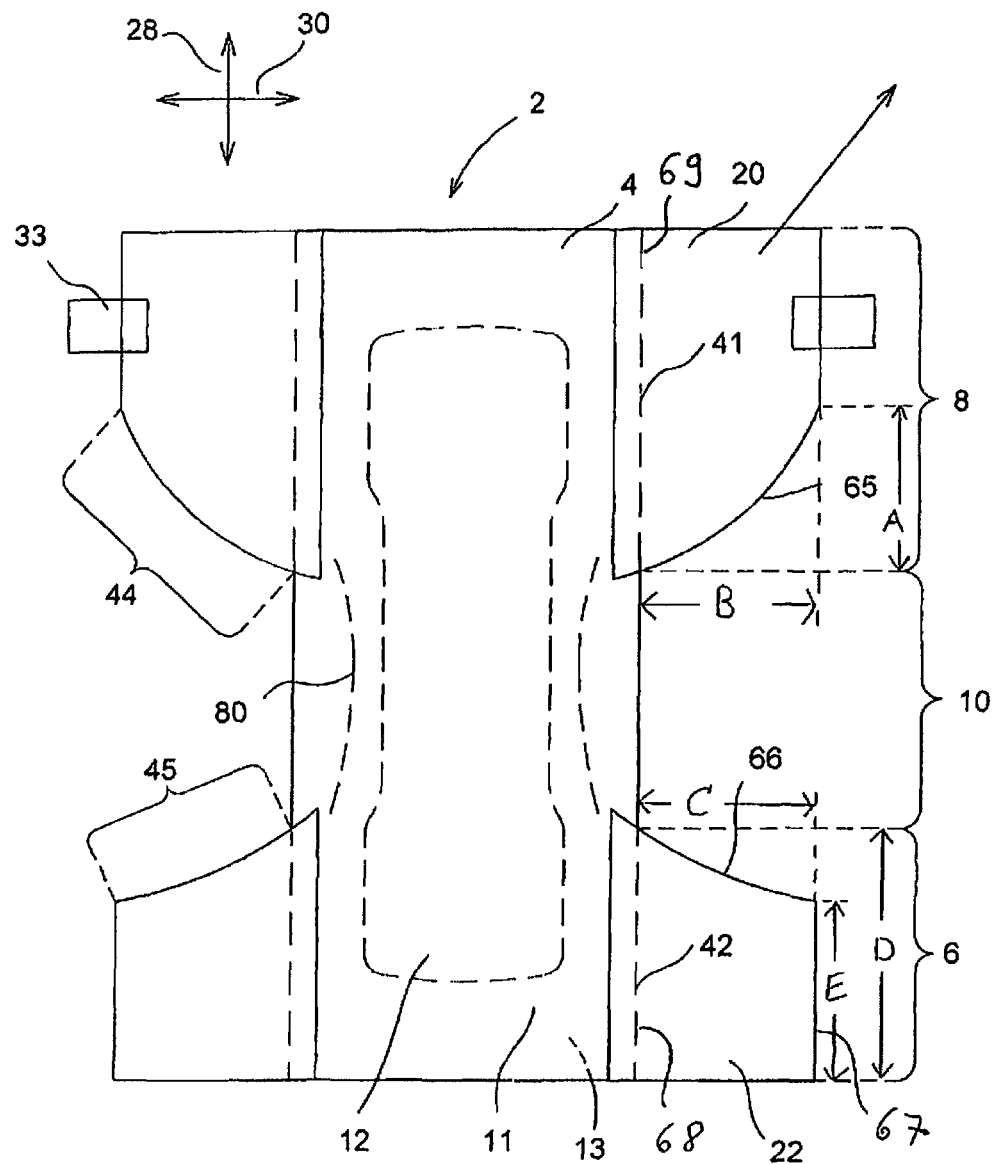
FIG. 1 shows a schematic illustration of a plan view, not to scale, of a disposable incontinence diaper produced by the method according to the invention, having diaper side parts attached on both sides.

FIG. 1 schematically shows, not to scale, a plan view of the inner side, that is to say the side facing the body, of a disposable absorbent incontinence diaper 2 according to the invention, of the open type (occasionally also referred to as diaper in the following text) in the just-unfolded state. The disposable incontinence diaper 2 comprises a diaper main part 4 having a front region 6, a rear region 8 and a crotch region 10 located in between in the longitudinal direction 28. Also indicated is an absorbent core 12, which is usually arranged between chassis-forming materials of the diaper main part 4, that is to say particularly between a liquid-permeable top sheet 11, which is formed from a nonwoven material, and a substantially liquid-impermeable back sheet 13, which is formed from a film material, of the diaper main part 4. The back sheet 13 can also be formed from a liquid-impermeable nonwoven or from a nonwoven-film laminate, with the nonwoven layer then coming to lie on the outside and the film layer on the inside in a manner directed toward the absorbent core. This gives the disposable incontinence diaper 2 a textile-like impression. Laterally next to the longitudinal edges of the absorbent core 12, first elastic elements 80 are attached to the diaper main part 4, between the top sheet 11 and the back sheet 13. The elastic elements 80 extend substantially in the longitudinal direction 28, that is to say with a substantial component in the longitudinal direction, wherein in the illustrated case they follow a curved course along the leg-opening region portion to be assigned to the crotch region 10.

The disposable incontinence diaper 2 furthermore comprises front diaper side parts 22 and rear diaper side parts 20, which are attached to the diaper main part 4 on both sides as four separate nonwoven components. The lower edge 65 of the rear diaper side parts 20 has a convex portion 44, while the upper edge of the front diaper side parts 22 has a concave portion 45. In the illustrated embodiment, it can be seen that the curved edges of the longitudinal portions are contoured after being severed from the diaper side-part web in such a way that each rear diaper side part has a lower edge 65 which has a single convex portion 44, and each front diaper side part 22 has an upper edge 66 which has a single concave portion 45. Furthermore, the convex portion 44 extends in the transverse direction 30 over the entire width B of the lower edge 65 of a rear side part 20 and the concave portion 45 extends in the transverse direction 30 over the entire width C of the upper edge 66 of a front side part 22. It can also be seen that an outer edge 67 of the front diaper side parts 22 has a shorter length E than a respective inner edge 68 having the length D. In the case illustrated, the longitudinal extent of the front diaper side parts 22 is 65% of the longitudinal extent of the rear diaper side parts 20. Thus, when the diaper is put onto the body of a person, there is enough room for fixing the closure means.

In the illustrated case, the length D of the inner edge 68 of the front diaper side parts 22 corresponds to the maximum extent of the front diaper side parts 22 in the longitudinal direction 28, and thus the length of the front diaper side parts 22. Also the length of the inner edge 69 of the rear diaper side parts 20 corresponds to the maximum extent of the rear diaper side parts 20 in the longitudinal direction 28, and thus the length of the rear diaper side parts 20. However, the contouring of the edge 65, 66, facing the leg opening, of the rear and front diaper side parts 20, 22 could be configured such that the maximum extent of the diaper side parts, as seen in the transverse direction, is located outside the inner edges 69, 68 of the rear and front diaper side parts 20, 22.

The diaper side parts 20, 22 are connected nondetachably to chassis-forming materials of the diaper main part 4, that is to say for example to the back sheet 13 and/or to the top sheet 11, in an overlapping region. The diaper side parts 20, 22 extend beyond the front and rear lateral longitudinal edges 42, 41 of the diaper main part in the transverse direction 30. In the context of the present invention, this is based on the understanding that the respective inner edge 69, 68 of the diaper side parts 22, 20 is formed by the transition to the diaper main part 4, and thus by the rear longitudinal edge 41 and front longitudinal edge 42, respectively, of the main part 4.

The front and read lateral longitudinal edges 42, 41 of the diaper main part are thus understood, within the context of the invention, as being those longitudinal edge regions of the diaper main part to which the diaper side parts are attached and beyond which the latter extend. The longitudinal extent of the front and rear side edges of the diaper main part 42, 41 thus define also the longitudinal extent of the front region 6 and the rear region 8 of the disposable incontinence diaper 2.

The diaper side parts 20, 22 are designed and intended to be connected together in the put-on state of the disposable incontinence diaper 2, in order to form a hip region of the diaper that is continuous in the circumferential direction. In this case, the diaper side parts 20, 22 provided on one side of the diaper main part 4 are in each case connected together. To this end, closure means 33, in particular having mechanical closure aids such as burr hooks, are provided on the rear diaper side parts 20 and can be secured in a detachable manner to the outer side of the front diaper side parts 22. Preferably, the closure means can also be secured in a detachable manner to the outer side of the diaper main part 4 and more preferably also to the outer side of the rear diaper side parts 20, such that the incontinence article can be matched very variably to the anatomical conditions of the wearer. Both the front diaper side parts 22 and the rear diaper side parts 20 are formed from a nonwoven material, in the illustrated case from a PP spunbonded nonwoven, Pegatex S, manufacturer: Pegas a.s., Primetická 86, 66904 Znojmo, CZ. The basis weight of the nonwoven material of the front and rear diaper side parts is 27 g/m$^2$. The fiber thickness of the fibers forming the nonwoven material is 2 dtex.

As can be seen from FIG. 1, the rear diaper side parts 20 have a larger surface extent that the front diaper side parts 22.

Figure 2:
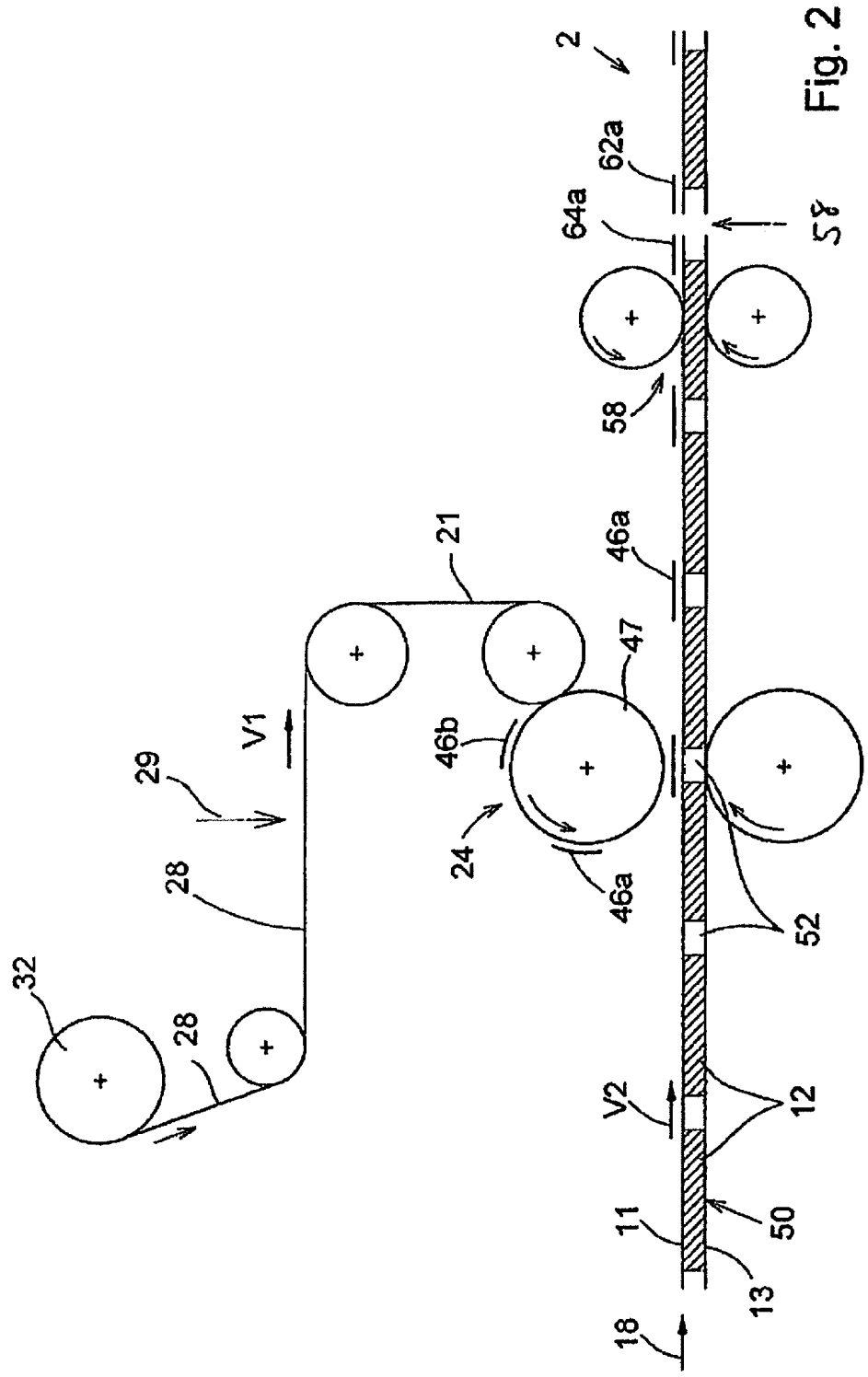
FIG. 2 shows a schematic illustration of the production method according to the invention.

FIG. 2 schematically illustrates a method according to the invention for producing a multiplicity of disposable incontinence diapers according to the invention.

In order to produce the diaper 2, according to FIG. 2 (upper region), a diaper side-part web 21 is formed and conveyed in the direction of a separating and application station 24. The diaper side-part web 21 comprises a web 28 that can be unwound endlessly from a feed roll 32 and consists of a substantially in particular non-extensible nonwoven material. At a tape station 29, indicated only schematically, closure tapes are attached to longitudinal edges of the web in a clocked manner, said closure tapes forming the subsequent closure means 33 of the diaper 2 (FIG. 1). The web 28 is conveyed further at the speed v1 in the direction of a separating and application station, provided overall with the reference sign 24, where successive first and second dual-use longitudinal portions 46*a*, 46*b* (that is to say ones which subsequently form in each case two sub-portions or in each case two diaper side parts) are severed from the diaper side-part web 21 and are accelerated to a speed v2 via a schematically indicated acceleration roller 47 and fed to the diaper main-part web 50.

Figure 6:
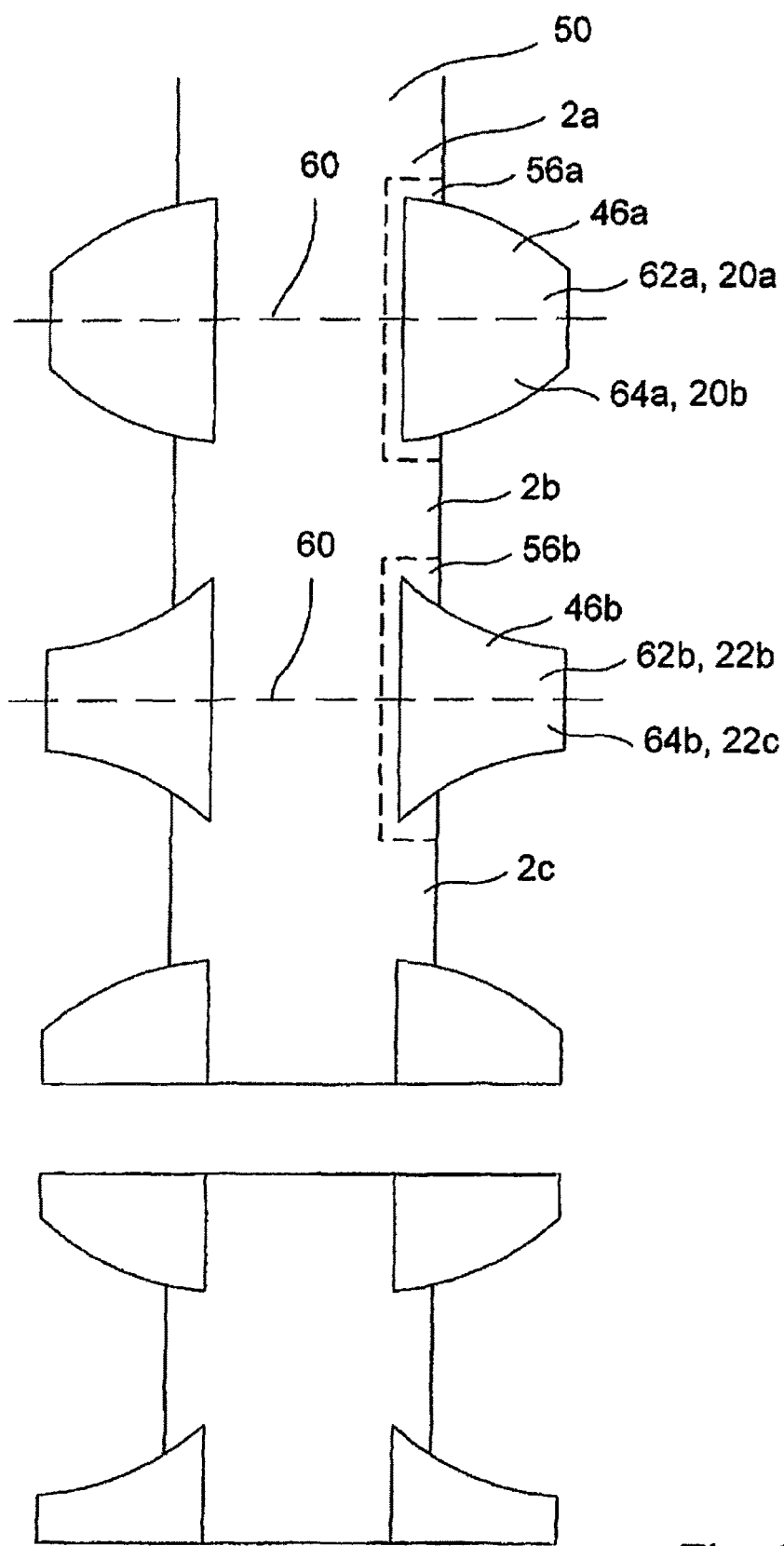
FIG. 6 shows a plan view of a diaper main-part web with applied dual-use longitudinal portions of a diaper side-part web.
Figure 9:
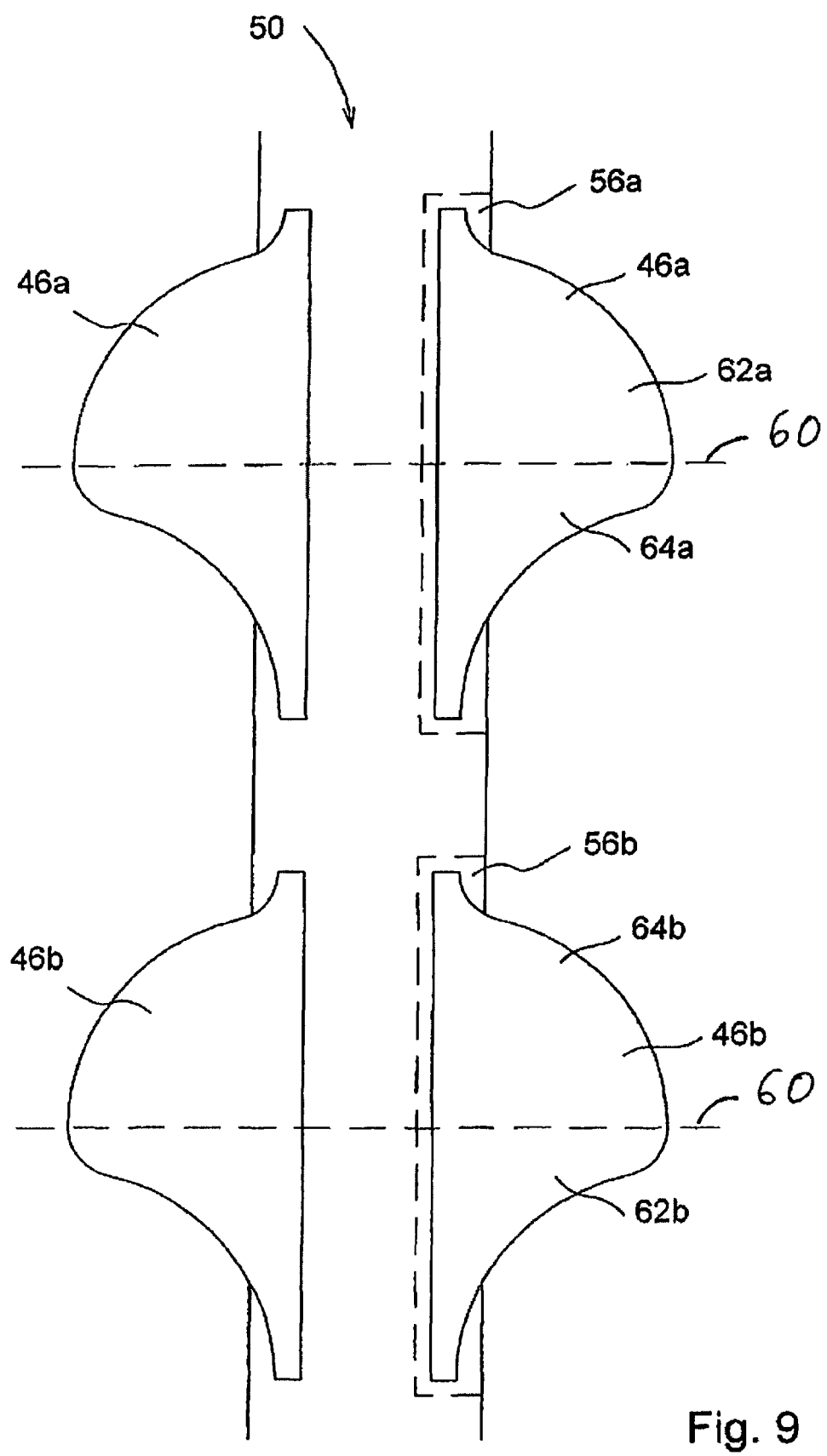
FIG. 9 shows a plan view of a diaper main-part web with applied dual-use longitudinal portions of a diaper side-part web according to FIG. 8.

The feeding and conveying of an endless diaper main-part web 50 is illustrated in the lower part of FIG. 2. The diaper main-part web 50 carries an endless number of successively deposited absorbent cores 12 that are spaced apart by intermediate spaces 52. Also indicated are a top-sheet layer 11 and a back-sheet layer 13. The absorbent core 12 and the top-sheet layer 11 are considered to belong to the diaper main-part web 50 in the following text. The diaper main-part web is conveyed endlessly at the speed v2 in the direction of the separating and application station 24. In the separating and application station 24, the longitudinal portions 46*a*, 46*b* of the diaper side-part web 22, as can be seen from FIG. 2, are applied to the diaper main-part web 50 and attached thereto, specifically such that, at the side edges of the main-part web 50, they extend over the subsequent separating lines 60 (see FIG. 6), along which the diapers are individually separated in a downstream method step, or are arranged in this region. This can be seen for example also in the plan view in FIGS. 6 and 9. In FIGS. 6 and 9, these longitudinal edge regions of the main-part web 50 are denoted by the reference sign 56*a* or 56*b*. The composite obtained in this way is conveyed further in the direction of the individual separating station 58, where a separating cut is carried out substantially transversely to the conveying direction, which corresponds to the longitudinal direction 18 of the diapers 2 to be produced, for example using a rotating cutter roller or using a punching tool. The separating cut or the separating line is indicated with the reference sign 60 in FIGS. 6 and 9. It is carried out such that it extends in each case through an applied longitudinal portion 46*a*, 46*b* and divides the latter into a respective first sub-portion 62*a*, 62*b* and in a respective second sub-portion 64*a*, 64*b*, which form the diaper side parts (see also FIGS. 6 and 9).

Figure 3:
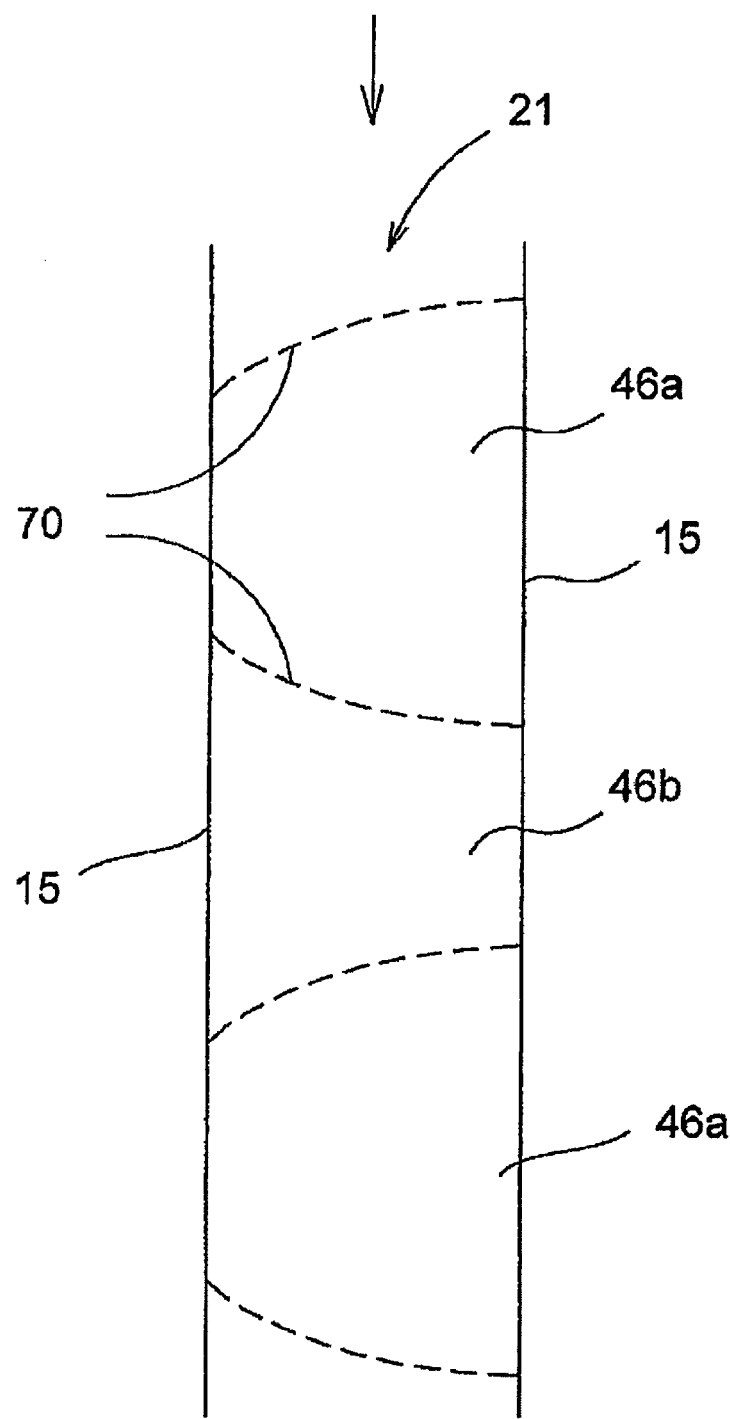
FIGS. 3 and 4 show a schematic illustration of a plan view of a diaper side-part web with indicated variants of the extent of separating line for severing dual-use longitudinal portions.
Figure 4:
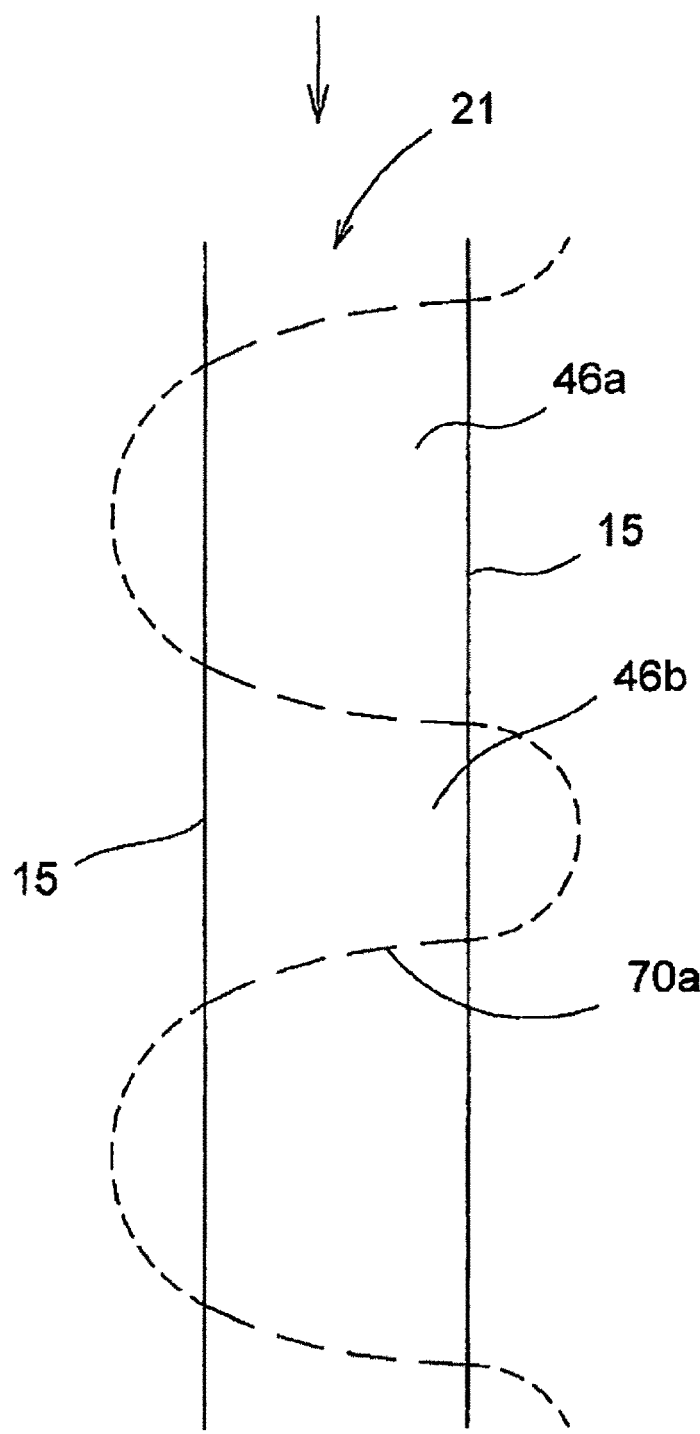
Figure 5:
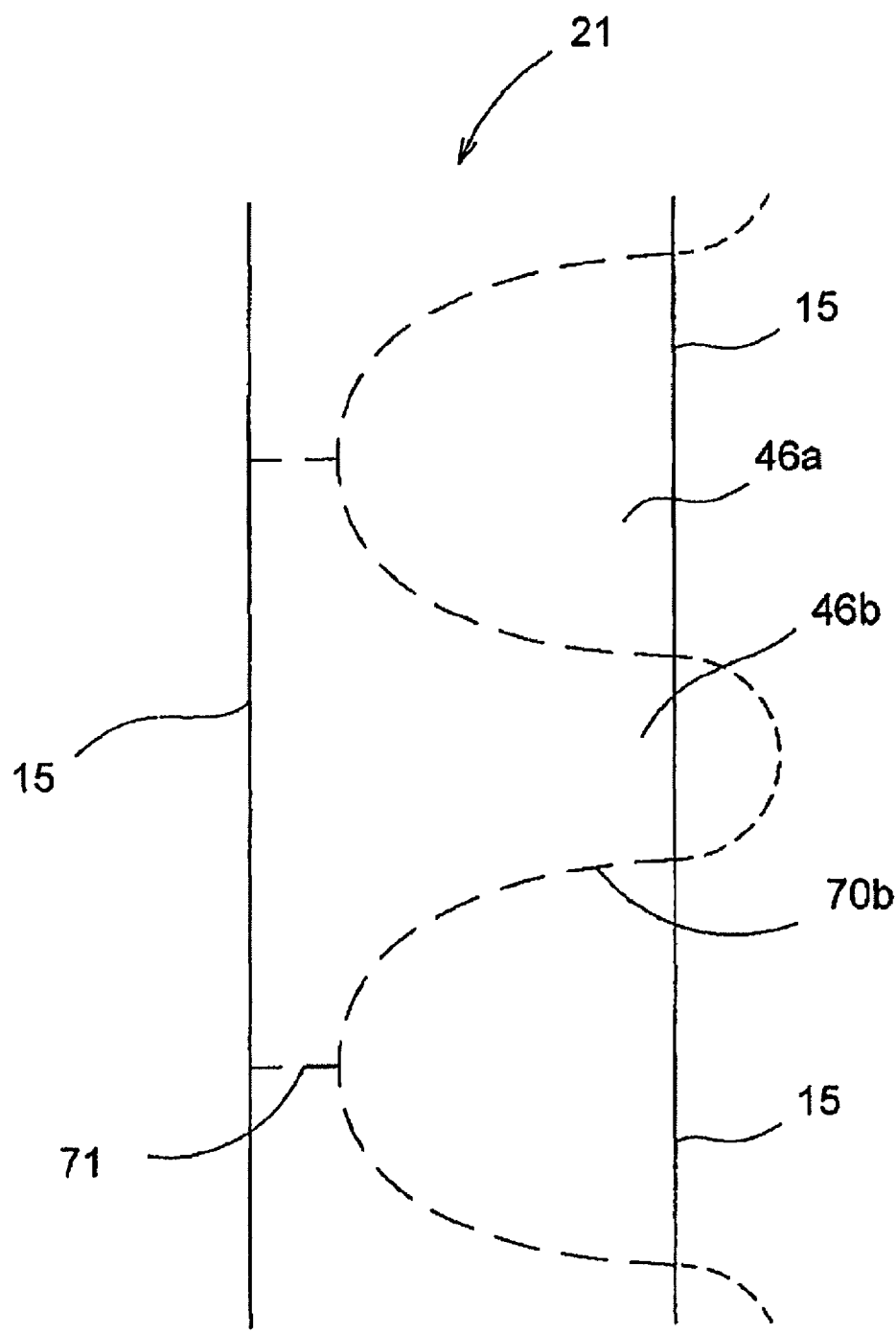
FIG. 5 shows a schematic illustration of a plan view of a diaper side-part web with a further indicated variant of the extent of separating lines for severing dual-use longitudinal portions.

Various method variants according to the invention will now be described with reference to FIGS. 3 to 9:

According to the method variant illustrated in FIG. 3, a diaper side-part web 21 is conveyed in the arrow direction. The arcuate separating lines 70, along which the first and second dual-use longitudinal portions 46*a*, 46*b* are severed can be seen, illustrated with dashed lines. It would also be conceivable and advantageous to carry out the severing of the longitudinal portions along a separating line 70*a* that extends in a wave-like or sinusoidal manner on both sides beyond the longitudinal edges 15 of the diaper side-part web 21 (FIG. 4). In an alternative variant of the method (FIG. 5), the severing takes place along a separating line 70*b* which extends in a wave-like or sinusoidal manner on one side, that is to say only beyond one of the longitudinal edges 15 of the diaper side-part web 21, such that the final severing of the second longitudinal portions 46*b* requires a further cut or a further punching operation, which then takes places substantially transversely to the longitudinal direction along a further separating line 71. This further separating operation can take placed in a temporally offset manner from or substantially at the same time as the first separating operation at an appropriately configured separating station.

FIG. 6 schematically shows a diaper main-part web 50, to which spaced-apart first longitudinal portions 46*a* and second longitudinal portions 46*b* of a diaper side-part web 21 have been attached on both sides of the web 50, and have been connected nondetachably to the diaper main-part web 50 for example by ultrasonic welding, by adhesive or in some other way. A separating cut or a separating line 60 for individually separating the diapers 2 is merely indicated in the upper part of FIG. 6, while in the lower part of FIG. 6 the individual separating station 58 (FIG. 2) has already been passed through and the separating cut 60 for individually separating the diapers has been carried out. In this case, in each case a first sub-portion 62*a*, 62*b* and a second sub-portion 64*a*, 64*b* are formed, wherein in the present case a first sub-portion 62*a* of a first longitudinal portion 46*a* forms a rear diaper side part 20*a* of a first diaper 2*a*, a second sub-portion 64*a* of a first longitudinal portion 46*a* forms a rear diaper side part 20*b* of a subsequent second diaper 2*b*, a first sub-portion 62*b* of a second longitudinal portion 46*b* forms a front diaper side part 22*a* of the second diaper 2*b*, and a second sub-portion 64*b* of a second longitudinal portion 46*b* forms a front diaper side part 22*c* of a subsequent third diaper 2*c*.

All of the diaper side parts on both sides of the diaper main part that are required for producing the diaper 2 can be provided by a single diaper side-part web. At the separating and application station illustrated schematically in FIG. 2, the severed longitudinal portions rotated or turned round as required and are positioned on the respective longitudinal edges of the diaper main part. However, it would also be conceivable and advantageous to feed two of the described diaper side-part webs to the diaper main-part web, in order to minimize or completely avoid the complexity of rotating and/or turning round the longitudinal portions and/or of positioning on both longitudinal edges of the main-part web.

Figure 7:
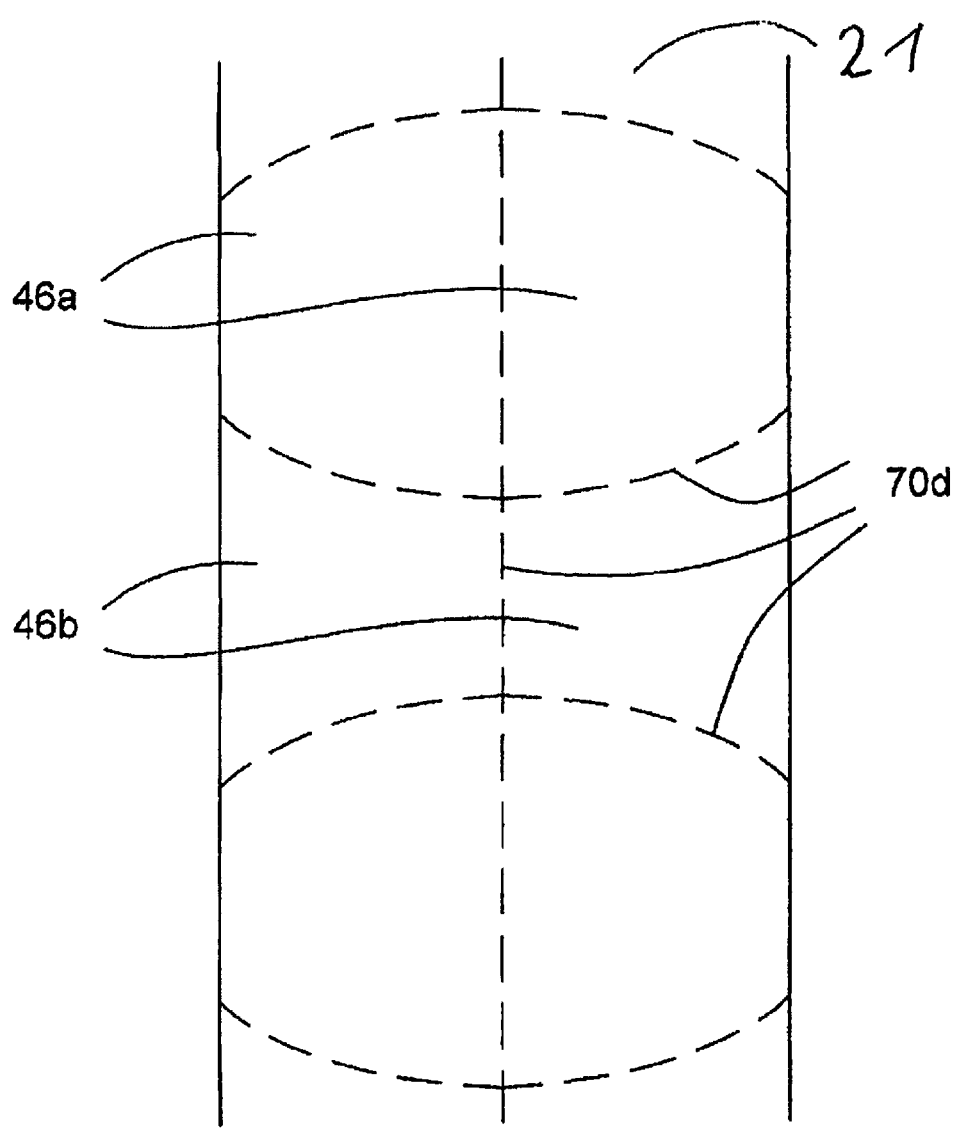
FIG. 7 shows a schematic illustration of a plan view of a diaper side-part web with a further indicated variant of the extent of separating lines for severing dual-use longitudinal portions.

According to a further variant which is shown in FIG. 7, in each case two dual-use first and second longitudinal portions 46*a*, 46*b* arranged alongside one another are severed from a single diaper side-part web 21, as seen in the transverse direction. The separating cuts which are required are indicated by dashed lines 70*d*.

In the variants illustrated in FIGS. 3-7 of the method according to the invention, a dual-use longitudinal portion consists of two sub-portions which form either rear diaper side parts or front diaper side parts.

Figure 8:
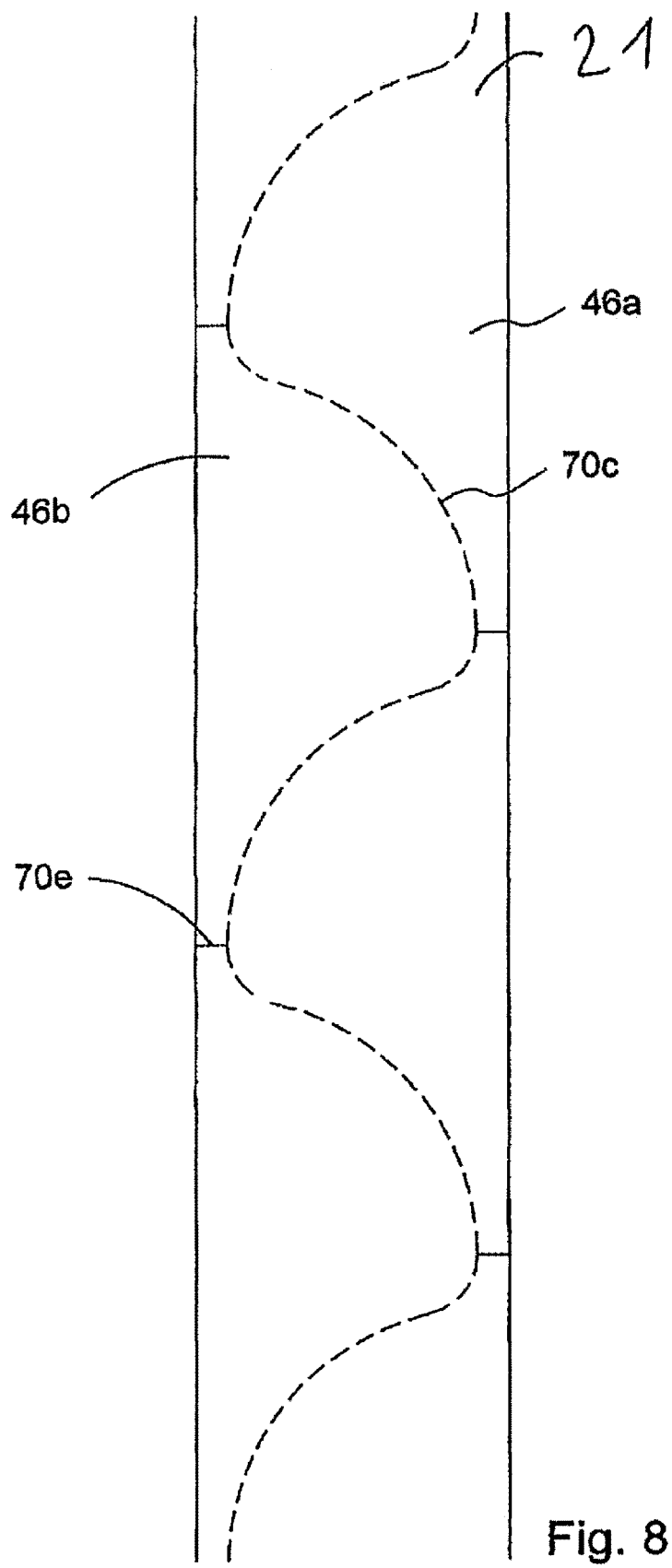
FIG. 8 shows a schematic illustration of a plan view of a diaper side-part web with a further indicated variant of the extent of separating lines for severing dual-use longitudinal portions.

In the further variant which is described in the following text, a dual-use longitudinal portion comprises in each case both a sub-portion which forms a rear diaper side part and a sub-portion which forms a front diaper side part. In FIG. 8, it can be seen that a separating line 70*c* extends in a sinusoidal or wave-like manner continuously through the diaper side-part web 21 with a component in the longitudinal direction. The web 21 could then first of all be divided into two part-webs along this separating line 70*c*, and only then would the dual-use longitudinal portions be severed by means of further transversely oriented separating cuts 70*e*. However, the separating operations could also take place substantially at the same time at a single separating and application station.

FIG. 9 schematically shows a diaper main-part web 50, to which spaced-apart first longitudinal portions 46*a* and second longitudinal portions 46*b* of the diaper side-part web 21 illustrated in FIG. 8 have been attached on both sides of the web 50, and have been connected nondetachably to the diaper main-part web 50 for example by ultrasonic welding, by adhesive or in some other way, at regions 56a, 56b of the longitudinal edge of the web. A respective separating cut or a separating line 60 for individually separating the diapers 2 is merely indicated in FIG. 9. It can be seen that the rear region of the diapers to be individually separated on the still endless web each adjoin the front region of the subsequent diaper. A respective longitudinal portion 46a, 46b is therefore divided by way of the cut for individually separating the diapers, such that in each case a sub-portion 62a, 64a, 62b, 64b forming a front and a rear diaper side part result from each longitudinal portion 46a, 46b.

The present invention has thus been successful in creating a cost-effective method that can be realized advantageously in terms of process technology, for producing an incontinence article for adults that has two separately attached rear diaper side parts and front diaper side parts, wherein the rear diaper side parts have a convex portion and the front diaper side parts have a concave portion.

The invention claimed is:

1. A method for producing a multiplicity of disposable incontinence diapers (2) having a diaper main part (4) and front and rear diaper side parts (22, 20) attached thereto, characterized by the following method steps of:
  feeding and conveying an endless diaper main-part web (50) in a first longitudinal direction (18) to a separating and application station (24);
  feeding an endless diaper side-part web (21) to the separating and application station (24), wherein, at the separating and application station (24), first and second dual-use longitudinal portions (46a, 46b) following one another and having at least regionally curved edges are severed from the diaper side-part web (21) and are attached to first and second regions (56a, 56b) of the diaper main-part web, wherein the first and second regions (56a, 56b) each comprise a hip region of two diaper main parts (4) following one another in the longitudinal direction and adjacent to one another;
  individually separating the disposable incontinence diapers (2) by separating the diaper main-part web (50) transversely to the first longitudinal direction (18), wherein the separating is carried out through the longitudinal portions (46a, 46b) such that a first sub-portion (62a) of at least one first respective longitudinal portion (46a) forms a rear diaper side part (20) of a first disposable incontinence diaper and a second sub-portion (64a) of the respective first longitudinal portion (46a) forms a front diaper side part (22) of an immediately adjacent second disposable incontinence diaper, and such that a first sub-portion (62b) of a second respective longitudinal portion (46b) forms a front diaper side part (22) of a disposable incontinence diaper and a second sub-portion (64b) of the respective second longitudinal portion (46b) forms a rear diaper side part (20) of an immediately adjacent further disposable incontinence diaper;
  wherein the curved edges of the longitudinal portions (46a, 46b) are contoured after being severed from the diaper side-part webs (21), such that, after the first and second longitudinal portions (46a, 46b) have been fixed to the first and second regions (56a, 56b) of the diaper main-part web, each rear diaper side part (20) has a lower edge (65) which has a convex portion, and each front diaper side part (22) has an upper edge (66) which has a concave portion, and such that the length E of an outer edge (67) of a respective front diaper side part (22) is shorter than the length D of an inner edge (68) of a respective front diaper side part (22); and
  wherein the longitudinal extent of the front diaper side parts (22) is at least 60% of the longitudinal extent of the rear diaper side parts (20).

2. The method as claimed in claim 1, characterized in that first elastic elements (80) that are made to extend in the first longitudinal direction (18) are attached to the diaper main-part web (50).

3. The method as claimed in claim 1, characterized in that the feeding of the diaper side-part web (21) to the separating and application station (24) takes place at a first speed v1 and the feeding of the endless diaper main-part web (50) to the separating and application station (24) takes place at a second speed v2, wherein the first speed v1 is lower than the second speed v2.

4. A method for producing a multiplicity of disposable incontinence diapers (2) having a diaper main part (4) and front and rear diaper side parts (22, 20) attached thereto, characterized by the following method steps of:
  feeding and conveying an endless diaper main-part web (50) in a first longitudinal direction (18) to a separating and application station (24);
  feeding an endless diaper side-part web (21) to the separating and application station (24), wherein, at the separating and application station (24), first and second dual-use longitudinal portions (46a, 46b) following one another and having at least regionally curved edges are severed from the diaper side-part web (21) and are attached to first and second regions (56a, 56b) of the diaper main-part web, wherein the first and second regions (56a, 56b) each comprise a hip region of two diaper main parts (4) following one another in the longitudinal direction and adjacent to one another;
  individually separating the disposable incontinence diapers (2) by separating the diaper main-part web (50) transversely to the first longitudinal direction (18), wherein the separating is carried out through the longitudinal portions (46a, 46b) such that a first sub-portion (62a) of at least one first respective longitudinal portion (46a) forms a rear diaper side part (20) of a first disposable incontinence diaper and a second sub-portion (64a) of the respective first longitudinal portion (46a) forms a rear diaper side part (20) of an immediately adjacent second disposable incontinence diaper, and such that a first sub-portion (62b) of a second respective longitudinal portion (46b) forms a front diaper side part (22) of a disposable incontinence diaper and a second sub-portion (64b) of the respective second longitudinal portion (46b) forms a front diaper side part (22) of an immediately adjacent further disposable incontinence diaper;
  wherein the curved edges of the longitudinal portions (46a, 46b) are contoured after being severed from the diaper side-part webs (21), such that, after the first and second longitudinal portions (46a, 46b) have been fixed to the first and second regions (56a, 56b) of the diaper main-part web, each rear diaper side part (20) has a lower edge (65) which has a convex portion, and each front diaper side part (22) has an upper edge (66) which has a concave portion, and such that the length E of an outer edge (67) of a respective front diaper side part (22) is shorter than the length D of an inner edge (68) of a respective front diaper side part (22);
  and wherein the longitudinal extent of the front diaper side parts (22) is at least 60% of the longitudinal extent of the rear diaper side parts (20).

5. A method for producing a multiplicity of disposable incontinence diapers (2) having a diaper main part (4) and front and rear diaper side parts (22, 20) attached thereto, characterized by the following method steps of:

feeding and conveying an endless diaper main-part web (50) in a first longitudinal direction (18) to a separating and application station (24);

feeding an endless diaper side-part web (21) to the separating and application station (24), wherein, at the separating and application station (24), first and second dual-use longitudinal portions (46a, 46b) following one another and having at least regionally curved edges are severed along separating lines (70, 70a, 70b, 70c, 70d, 70e, 71) from the diaper side-part web (21) and are attached to first and second regions (56a, 56b) of the diaper main-part web, wherein the first and second regions (56a, 56b) each comprise a hip region of two diaper main parts (4) following one another in the longitudinal direction and adjacent to one another;

individually separating the disposable incontinence diapers (2) by separating the diaper main-part web (50) transversely to the first longitudinal direction (18), wherein the separating is carried out through the longitudinal portions (46a, 46b) such that a first sub-portion (62a) of at least one first respective longitudinal portion (46a) forms a rear diaper side part (20) of a first disposable incontinence diaper and a second sub-portion (64a) of the respective first longitudinal portion (46a) forms a front or rear diaper side part (22, 20) of an immediately adjacent second disposable incontinence diaper, and such that a first sub-portion (62b) of a second respective longitudinal portion (46b) forms a front diaper side part (22) of a disposable incontinence diaper and a second sub-portion (64b) of the respective second longitudinal portion (46b) forms a front or rear diaper side part (22, 20) of an immediately adjacent further disposable incontinence diaper;

wherein the curved edges of the longitudinal portions (46a, 46b) are contoured after being severed from the diaper side-part webs (21), such that, after the first and second longitudinal portions (46a, 46b) have been fixed to the first and second regions (56a, 56b) of the diaper main-part web, each rear diaper side part (20) has a lower edge (65) which has a convex portion, and each front diaper side part (22) has an upper edge (66) which has a concave portion, and such that the length E of an outer edge (67) of a respective front diaper side part (22) is shorter than the length D of an inner edge (68) of a respective front diaper side part (22);

and wherein the longitudinal extent of the front diaper side parts (22) is at least 60% of the longitudinal extent of the rear diaper side parts (20).

6. The method as claimed in claim 5, characterized in that one separating line (70c) extends in a sinusoidal or wave-like manner through the material of the diaper side-part web (21) and thereby divides the diaper side-part web (21) into two part-webs.

7. The method as claimed in claim 5, characterized in that one separating line (70, 70a, 70b, 70d) extends in a sinusoidal or wave-like or arcuate manner on one or both sides beyond the longitudinal edges of the diaper side-part web (21).

\* \* \* \* \*